United States Patent [19]

Karol et al.

[11] Patent Number: 4,482,464

[45] Date of Patent: Nov. 13, 1984

[54] HYDROCARBYL-SUBSTITUTED MONO- AND BIS-SUCCINIMIDE HAVING POLYAMINE CHAIN LINKED HYDROXYACYL RADICALS AND MINERAL OIL COMPOSITIONS CONTAINING SAME

[75] Inventors: Thomas J. Karol, Wappingers Falls; Raymond C. Schlicht, Fishkill; Harold S. Magaha, Wappingers Falls, all of N.Y.

[73] Assignee: Texaco Inc., White Plains, N.Y.

[21] Appl. No.: 465,941

[22] Filed: Feb. 14, 1983

[51] Int. Cl.³ .............................................. C10M 1/36
[52] U.S. Cl. ........................... 252/51.5 A; 252/52.5 R
[58] Field of Search ...................... 252/51.5 A, 51.5 R

[56] References Cited

U.S. PATENT DOCUMENTS 3,172,892  3/1965  LeSuer et al. ................. 252/51.5 A
3,185,704  5/1965  Kahn et al. .................... 252/51.5 A
4,048,080  9/1977  Lee et al. ...................... 252/51.5 R

*Primary Examiner*—Jacqueline V. Howard
*Attorney, Agent, or Firm*—Robert A. Kulason; James J. Young; James J. O'Loughlin

[57] ABSTRACT

A hydrocarbyl-substituted mono- and bis-succinimide having polyamine chain linked hydroxyacyl radicals represented by the formula:

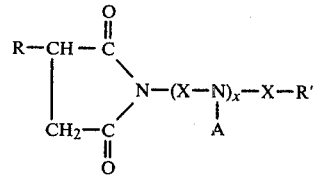

in which R is a hydrocarbyl radical having from about 8 to 400 carbon atoms, X is a divalent alkylene or secondary hydroxy-substituted alkylene radical having from 2 to 3 carbon atoms, A is hydrogen or a hydroxyacyl radical from the group consisting of glycolyl, lactyl, 2-hydroxymethyl propionyl and 2,2′-bis-hydroxymethyl propionyl radicals and in which at least 30 percent of said radicals represented by A are said hydroxyacyl radicals, x is a number from 1 to 6, and R′ is a radical selected from the group consisting of —NH₂, —NHA, or a hydrocarbyl substituted succinyl radical having the formula:

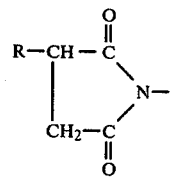

in which R and A have the values noted above, and a hydrocarbon oil composition containing same are provided.

17 Claims, No Drawings

HYDROCARBYL-SUBSTITUTED MONO- AND BIS-SUCCINIMIDE HAVING POLYAMINE CHAIN LINKED HYDROXYACYL RADICALS AND MINERAL OIL COMPOSITIONS CONTAINING SAME

BACKGROUND OF THE INVENTION

1. Field of the Invention

Internal combustion engines operate under a wide range of temperatures including low temperature stop-and-go service as well as high temperature conditions produced by continuous high speed driving. Stop-and-go driving, particularly during cold, damp weather conditions, leads to the formation of a sludge in the crankcase and in the oil passages of a gasoline or a diesel engine. This sludge seriously limits the ability of the crankcase oil to effectively lubricate the engine. In addition, the sludge with its entrapped water tends to contribute to rust formation in the engine. These problems tend to be aggravated by the manufacturer's lubrication service recommendations which specify extended oil drain intervals.

It is known to employ nitrogen containing dispersants and/or detergents in the formulation of crankcase lubricating oil compositions. Many of the known dispersant/detergent compounds are based on the reaction of an alkenylsuccinic acid or anhydride with an amine or polyamine to produce an alkylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a product having a relatively high level of nitrogen in order to provide improved dispersancy in a crankcase lubricating oil composition.

With the introduction of four cylinder internal combustion engines which must operate at relatively higher engine speeds or rpm's than conventional 6- and 8-cylinder engines in order to produce the required torque output, it has become increasingly difficult to provide a satisfactory dispersant lubricating oil composition.

Another problem facing the lubricant manufacturer is that of seal deterioration in the engine. All internal combustion engines use elastomer seals, such as Viton seals, in their assembly. Over time, these seals are susceptible to serious deterioration caused by the lubricating oil composition. A lubricating oil composition that degrades the elastomer seals in an engine is unacceptable to engine manufacturers and has limited value.

It is an object of this invention to provide a novel lubricating oil additive.

Another object is to provide a novel lubricating oil composition which does not degrade elastomer seals in internal combustion engines.

A still further object is to provide a lubricating oil composition which can withstand the stresses imposed by modern internal combustion engines.

2. Description of the Prior Art

U.S. Pat. Nos. 3,172,892 and 4,048,080 disclose alkenylsuccinimides formed from the reaction of an alkenylsuccinic anhydride and an alkylene polyamine and their use as dispersants in a lubricating oil composition.

U.S. Pat. No. 2,568,876 discloses reaction products prepared by reacting a monocarboxylic acid with a polyalkylene polyamine followed by a reaction of the intermediate product with an alkenyl succinic anhydride.

U.S. Pat. No. 3,216,936 discloses a process for preparing an aliphatic amine lubricant additive which involves reacting an alkylene amine, a polymer substituted succinic acid and an aliphatic monocarboxylic acid.

U.S. Pat. No. 3,131,150 discloses lubricating oil compositions containing dispersant-detergent mono- and di-alkyl-succinimides or bis(alkenylsucinimides).

Netherlands Pat. No. 7,509,289 discloses the reaction product of an alkenylsuccinic anhydride and an aminoalcohol, namely a tris(hydroxymethyl)-aminomethane.

Copending application Ser. No. 334,774, filed on Dec. 28, 1981, discloses a hydrocarbyl-substituted succinimide dispersant having a secondary hydroxy-substituted diamine or polyamine segment and a lubricating oil composition containing same.

U.S. Pat. No. 4,338,205 discloses alkenyl succinimide and borated alkenyl succinimide dispersants for a lubricating oil with impaired diesel dispersancy in which the dispersant is treated with an oil-soluble strong acid.

The disclosures of U.S. Pat. No. 3,172,892, U.S. Pat. No. 4,048,080 and of application Ser. No. 334,774 are incorporated herein by reference.

SUMMARY OF THE INVENTION

The novel hydrocarbyl-substituted mono- and bis-succinimide having polyamine chain linked hydroxyacyl radicals of the invention is represented by the formula:

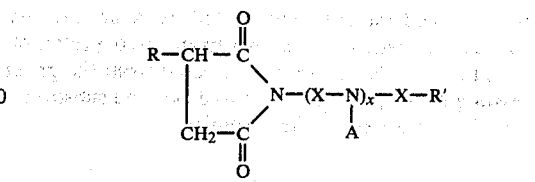

in which R is a hydrocarbyl radical having from about 8 to 400 carbon atoms, X is a divalent alkylene or secondary hydroxy-substituted alkylene radical having from 2 to 3 carbon atoms, A is hydrogen or a hydroxyacyl radical from the group consisting of glycolyl, lactyl, 2-hydroxymethyl propionyl and 2,2'-bis-hydroxy methyl propionyl radicals and in which at least 30 percent of said radicals represented by A are hydroxyacyl radicals, x is a number from 1 to 6, and R' is a radical selected from the group consisting of $-NH_2$, $-NHA$, or a hydrocarbyl substituted succinyl radical having the formula:

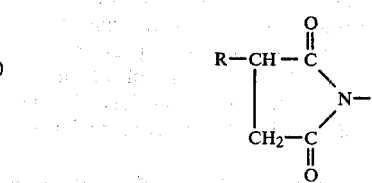

in which R and A have the values noted above.

The prescribed succinimide which inhibits elastomer seal deterioration is prepared by reacting a hydrocarbylsubstituted succinimide precursor with an excess of an acylating agent from the class consisting of glycolic acid, lactic acid, 2-hydroxymethyl propionic acid and 2,2'-bis-hydroxymethyl propionic acid. This reaction is continued until at least thirty percent of the reactive nitrogen atoms in the succinimide have reacted with the hydroxy acid acylating agent to form amides.

The hydrocarbon oil composition of the invention, comprises a mineral oil base and the prescribed hydrocarbyl-substituted mono- and bis-succinimide having polyamine chain linked or pendant hydroxyacyl radicals.

DESCRIPTION OF THE PREFERRED EMBODIMENTS

The hydrocarbyl-substituted mono- and bis-succinimide having polyamine chain linked hydroxyacyl radicals of the invention is represented by the formula:

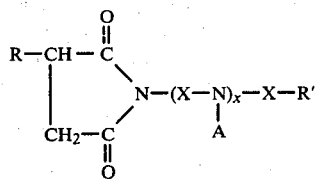

in which R is a hydrocarbyl radical having from about 8 to 400 and preferably an alkyl radical having from 50 to 200 carbon atoms, X is a divalent alkylene or secondary hydroxy-substituted alkylene radical having from 2 to 3 carbon atoms, A is hydrogen or a hydroxyacyl radical from the group consisting of glycolyl, lactyl, 2-hydroxymethyl propionyl and 2,2'-bis-hydroxymethyl propionyl radicals and in which at least 30 percent of said radicals represented by A are said hydroxyacyl radicals, x is a number from 1 to 6, preferably from 2 to 4, and R' is a radical selected from the group consisting of $NH_2$, —NHA or a hydrocarbyl substituted succinyl radical having the formula:

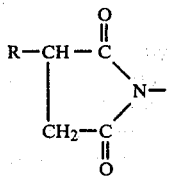

in which R and A have the values noted above.

It is essential that at least thirty percent of the reactive nitrogen atoms in the succinimide chain form an amide with the prescribed hydroxyacyl radical in order to provide a dispersant which inhibits the deterioration of elastomer or Viton engine seals. It is preferred that at least fifty percent, i.e. from 50 to 100 percent, of the reactive nitrogen atoms be reacted with a hydroxy aliphatic acid to form the amide. The most preferred compounds are those in which substantially all of the reactive nitrogens in the succinimide chain have been reacted such as from about 85 to 100 percent, to form the prescribed amides.

Particularly effective hydroxyacylated hydrocarbyl-substituted monosuccinimides are those prepared from an alkenylsuccinimide and glycolic acid. This hydroxyacylated monosuccinimide is represented by the formula:

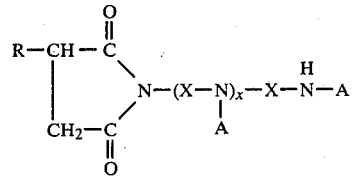

in which R is a monovalent alkenyl radical having from about 50 to 200 carbon atoms, preferably 80 to 150 carbon atoms, X is a divalent alkylene or secondary hydroxy-substituted alkylene radical having from 2 to 3 carbon atoms, x is a number from 1 to 6 and preferably from 2 to 4, and A is a glycolyl radical in which from 85 to 100 percent of said reactive nitrogen atoms have been reacted to form amides with the noted glycolyl radicals.

A preferred bis-hydrocarbylsuccinimide of the invention is represented by the formula:

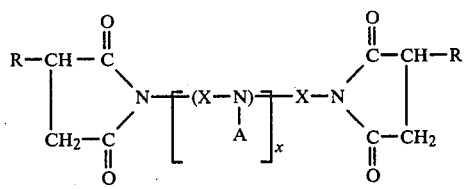

in which R, X and A have the values noted above.

The hydrocarbyl-substituted mono- and bis-succinimide having polyamine chain linked or pendant hydroxyacyl radicals of the invention is prepared by reacting a hydrocarbylsuccinimide or hydrocarbyl-substituted bis-succinimide with the prescribed hydroxyaliphatic acid and effecting a reaction under acylating conditions. The amount of hydroxyacylating agent employed is an amount necessary to react with at least thirty percent of the reactive nitrogen atoms in the succinimide chain. Preferably, the amount of hydroxyacylating agent employed will be an amount which can react with from 50 to 100 percent of the reactive nitrogen atoms in the succinimide chain to effect the formation of amides. Amounts of hydroxyacylating agent approximately stoichiometrically equivalent in moles to the amount of reactive nitrogen atoms present in the succinimide chain or excess amounts of said agent are suitable. The hydroxyacylating agent and the reactive nitrogen moieties in the succinimide are reacted until the prescribed amount of amidation has taken place. Hydrocarbyl-substituted mono- and bis-succinimide are well known in the art and their preparation does not constitute a part of this invention.

The compounds which can be employed for preparing the prescribed succinimide of the invention are hydroxy aliphatic acids from the class consisting of glycolic acid, lactic acid, 2-hydroxymethyl propionic acid and 2,2'-bis-hydroxymethyl propionic acid. It is understood that equivalents of the aliphatic acids prescribed namely their anhydrides and acyl halides can also be employed in the practice of this invention. A characteristic of the prescribed $C_2$ and $C_3$ hydroxyaliphatic carboxylic acids is their relatively limited or negligible solubility in mineral oil.

The prescribed succinimide of the invention is generally employed in a mineral oil or in a lubricating oil composition at a concentration ranging from about 0.01 to 10 weight percent and preferably at a concentration ranging from about 0.5 to 5 weight percent based on the total weight of the composition. Broader concentrations from 0.001 to 80 percent can also be employed.

The following examples illustrate the preparation of specific hydrocarbyl-substituted mono- and bis-succinimides having branched hydroxyacyl radicals and their utility and effectiveness in preventing, the deterioration of elastomer engine seals.

EXAMPLE I

Glycolic Acid Mono-Amide of a Polybutenyl-succinimide of a Secondary Hydroxy-Substituted Polyamine (SHPA)

A 6300 g (0.9 mole) quantity of a 50% oil concentrate of a polybutenylsuccinimide prepared from an approximately 1300 mol. wt. polybutenylsuccinic acid anhydride (PBSA) and a secondary-hydroxy substituted polyamine (SHPA)[1] in 0.9:1 mole ratio[2], respectively, is preheated to 90°, and 97.50 g. (0.9 mole) of an aqueous glycolic acid solution (70% conc.) is then added. The mixture is heated with $N_2$-blowing to 160° where it is held for 3-4 hrs. while distilling out water until the mixture is essentially dry and has a significantly reduced acid content (total acid No.=4). The crude product is then polish-filtered before use. The yield of final product was 6143 g; the analytical results were:

% N=0.96, Total Acid Number (TAN)=3.9, and a Total Base Number (TBN)=13.5.

[1] Prepared by reaction of ethylenediamine and epichlorohydrin.
[2] Based on nitrogen content assuming 4 nitrogen atoms per mole.

EXAMPLE II

Preparation of a Glycolic Acid Amide via a One-Pot Process, starting with the PBSA and SHPA used in the Previous Example The mixture of 237.6 g (1.35 mole) of a secondary hydroxy polyamine (SHPA) prepared by reaction of epichlorohydrin and ethylenediamine and 2255.5 g of a diluent mineral oil (about 100 SUS at 100° F.) was heated to 60° and 37.5 g (1.5 mole) of a polybutenylsuccinic acid anhydride (also containing free polybutene and about 20% of the diluent oil is added under a $N_2$ atmosphere over 0.5 hr. The mixture is then heated to 110° C. to essentially complete the initial reaction of the amine and the PBSA. After 0.5 hr. at 110°, 124.9 g (1.15 mole) of aqueous glycolic acid (70% conc.) is added. The final mixture is heated with more rapid $N_2$-blowing to 160°, distilling out the water. After 3 hrs. at 160°, the product is filtered through diatomaceous earth to recover 6035 g of product; the analyses were: % N=0.99, TAN=0.55, TBN=14.6.

Additional examples of amide derivatives of polybutenyl(1300 mol. wt.) succinimides of secondary hydroxysubstituted polyamines are illustrated in Table I below:

TABLE I

Acid Amides of Secondary Hydroxy-Substituted Polybutylenesuccinimides[1]

| Ex. No | SHPA:PIBSA Mole Ratio | Acid Reactant Name | Moles[2] | % N | TAN | TBN |
|---|---|---|---|---|---|---|
| III | 0.9:1 | Glycolic | 3.5 | 0.97 | 1.2 | 5.6 |
| IV | 0.9:1 | Glycolic | 1.33 | 0.92 | 0.7 | 10.7 |
| V | 0.9:1 | Lactic | 1.0 | 0.90 | 0.3 | 16.6 |
| VI | 0.9:1 | 2,2'-Bis-hydroxymethyl-propionic | 1.33 | 0.96 | 4.3 | 16.9 |
| VII | 0.65:1 | Glycolic | 1.0 | 0.67 | 1.0 | 6.1 |

[1] The Example I procedure was varied by the addition of 80 ml-xylene per 100 g. of oil concentrate of the succinimide; reaction was carried out at xylene reflux at 140-160° C.
[2] Mole ratio of acid:succinimide based on 4 N atoms calculated per mole of succinimide.

The dispersancy properties of the amides disclosed in Table I above were determined in the Bench VC Test after they were added to a conventional 10W-40 motor oil formulation at concentrations ranging from 4.5 to 10 weight percent. The results of these tests are set forth in Table II.

TABLE II

BENCH DISPERSANCY TESTS ON HYDROXY ACID AMIDES OF SHPA IMIDES

| Dispersant Example No. | BVCT Results, @, wt % | | Reference Oils | | |
|---|---|---|---|---|---|
| | 5.0 | 6.5 | PV 9.14 | FREO 200-3 | PV-911 |
| I | 13.0 | 10.0 | 9.0 | 15.0 | 63.5 |
| II | 9.4 | 9.5 | 8.4 | 28.2 | 59.5 |
| III | 8.0 | 7.5 | 9.5 | 12.5 | 60.5 |
| IV | 6.0 | 5.0 | 6.0 | 10.0 | 52.0 |
| V | 10.3 | 7.7 | 9.9 | 31.3 | 69.9 |

An important property of a lubricating oil additive and a blended lubricating oil composition containing additives is the compatibility of the oil composition with the rubber seals employed in the engine. Nitrogen-containing succinimide dispersants employed in crankcase lubricating oil compositions have the effect of seriously degrading the rubber seals in internal combustion engines. In particular, such dispersants are known to attack Viton AK-6 rubber seals which are commonly employed in internal combustion engines. This deterioration exhibits itself by sharply degrading the flexibility of the seals and in increasing their hardness. This is such a critical problem that the Daimler-Benz Corporation requires that all crankcase lubricating oils must pass a Viton Seal Compatibility Test before the oil composition will be rated acceptable for engine crankcase service. The AK-6 Bend Test is described below and is designed to test the Viton seal compatibility of a crankcase lubricating oil composition containing a nitrogen-containing dispersant.

The AK-6 Bend Test is conducted by soaking a sample of Viton AK-6 rubber at an elevated temperature in the oil being tested then determining the bending properties and hardness of the Viton rubber sample against a suitable sample. Specifically, a 38 by 9.5 mm slab of a Viton AK-6 rubber cut with the grain of the rubber is placed in a 30 ml wide-mouth bottle with 20 ml of the test oil. The bottle is sealed and the test sample placed in an oven at 149° C. for 96 hours. The bottle is removed from the oven and the rubber specimen taken from the initial bottle and placed into a second bottle with a new charge of test oil. After 30 minutes in the new oil charge, the rubber specimen is removed from the second bottle and submitted to a Bend Test. This is done by bending the rubber specimen 180°. The degree of cracking is observed and reported as follows: no cracking (NC) surface cracking (SC) or cracking (C). If cracking is observed, the test is terminated on that particular sample.

If no cracking has been observed, the rubber specimen is returned to the bottle containing the second oil charge and this bottle is returned to the oven maintained at 149° C. After an additional 72 hours of soaking in the test oil at 149° C., the bottle is removed from the oven and the rubber specimens withdrawn and placed into another bottle containing a fresh oil charge for 30 minutes, following which the bend test is repeated.

If the rubber specimen continues to pass the bend test, the test is continued for 2 more heat-soak cycles of 96 hours and 72 hours respectively, each heat-soak cycle being followed by the bend test for total test time of 336 hours from the time the specimens were initially put into the oven.

Following the above procedure, each rubber specimen is removed from its bottle, washed in naphtha to remove all oil traces and then air dried. The rubber specimens are then submitted to a hardness test according to the procedure described in ASTM D2240 following which a final bend test is made on all specimens.

The Viton compatibility of hydroxy acid amides of secondary hydroxy-substituted polyaminesuccinimides was determined by blending 7.0 weight percent of the dispersant composition (3.5 wt. % active succinimide concentration) into an SAE 10W-30 oil formulation. The results of the Viton compatibility testing are set forth in the table below:

TABLE III

VITON COMPATIBILITY OF HYDROXYACID AMIDES OF SHPA SUCCINIMIDES

| Dispersant EX. No. | AK-6 Bend Test[1] Cracked at, hrs.[2] |
|---|---|
| Reference[3] | Slight at 168 |
| I | None at 336[a] |
| II | Slight at 336[a] |
| III | None at 336[a] |
| V | None at 336[a] |
| VI | Slight at 264 |
| VII | None at 336[a] |

[1]The additives were blended at 7% wt. (3.5% active concentration) into an SAE 10W-30 oil formulation.
[2]Slight cracking is considered borderline acceptable.
[3]The non-acylated succinimide corresponding to Examples I through VI.

The acylated product of Example II which employed glycolic acid as the acylating agent was blended into an SAE 10W-30 oil formulation of a concentration of 3 wt. % (1.5% active dispersant concentration) and submitted to the following tests:

TABLE IV

| FURTHER TESTING OF THE EXAMPLE II PRODUCT | |
|---|---|
| | Result |
| Daimler-Benz Viton Seal Compatibility Sequence VD Test (SF limits) | Pass |
| Avg. sludge (9.4 min) | 9.60 |
| Avg. varnish (6.6 min) | 5.6 |
| Piston skirt varnish (6.7 min) | 6.5 |
| CRC L-38 (40 max) | 14.9 |

The above results indicate that the subject dispersant example provided acceptable seal-compatibility, gasoline engine sludge dispersancy, and is non-corrosive to copper lead bearings.

Glycolic acid derivatives of polyethylene amine succinimide dispersants also show improvement in fluoroelastomer compatibility and dispersancy over the non-acylated succinimides. A typical preparation of a glycolic acid product is shown below.

EXAMPLE VIII

In a typical preparation, 3237 g (1.5 mol) of polybutenylsuccinic anhydride was added to a stirring mixture of 255 g (1.35 mole) of TEPA and 3014 g of diluent oil. After heating for ca 1 hour at 110° C. under a nitrogen atmosphere, 544 g (4.73 mol) of a 66% solution of glycolic acid in water was added to the reaction flask. The mixture was heated to 160° C. with removal of water by distillation. After holding at 160° for 4 hours the mixture was filtered to give the desired product: %N=1.2; TAN, D-664=17.9; TBN, D-2896=14.4.

Other glycolic acid derivatives were synthesized using the procedure detailed above but with various amines and various amounts of PBSA, amine and glycolic acid. These derivatives are listed in Table V.

TABLE V

Glycolic Acid Derivatives of Polyethyleneamine Succinimides

| | | PBSA:Amine: | Analyses | | |
|---|---|---|---|---|---|
| Example | Amine | Glycolic Acid | % N | TAN | TBN |
| IX | TETA | 1.0:0.9:1.0 | 1.0 | — | 11.4 |
| X | TETA | 1.0:0.9:2.0 | 1.0 | — | 8.3 |
| XI | TETA | 1.0:0.9:3.0 | 1.0 | — | — |
| XII | TEPA | 1.0:0.9:3.0 | 1.3 | 8.9 | 13.2 |
| XIII | TEPA | 1.0:0.9:2.5 | 1.2 | 5.0 | 15.2 |
| XIV | TEPA | 1.0:0.55:2.5 | 0.8 | 10.3 | 7.7 |
| XV | TEPA | 1.0:0.55:1.5 | 0.8 | 1.9 | — |

Substantial improvement in the fluoroelastomer compatibility and in dispersancy is obtained with the glycolic acid derivatives as shown in Tables VI and VII.

TABLE VI

DB Viton Compatibility of Glycolic Acid of Polyethyleneamine Succinimides[1]

| Example | % Elongation | Tensile Strength | Cracking |
|---|---|---|---|
| VIII | 167 | 5.9 | None |
| X | 67 | 8.5 | None |
| XI | 177 | 7.5 | None |
| XIII | 200 | 9.0 | None |
| XIV | 195 | 10.0 | None |
| Non-acylated TETA succinimide | 33 | 5.4 | Yes |

[1]SAE 10W-30 motor oil formulations containing 70% dispersant.

TABLE VII

BVC Testing of Glycolic Acid Derivatives of Polyethyleneamine Succinimides[1]

| | BVCT | | Reference Oils | | |
|---|---|---|---|---|---|
| Example | 4% | 6% | PV-914 | FREO 200-3 | PV911 |
| VIII | 10.0 | 7.6 | 19.0 | 29.5 | 44.0 |
| IX | 56.2 | 17.3 | 8.4 | 16.8 | 74.4 |
| X | 49.0 | 11.0 | 6.5 | 12.0 | 59.0 |
| XI | 24.0 | 8.5 | 6.5 | 12.0 | 59.0 |
| XIII | 19.2 | 10.9 | 5.9 | 24.6 | 44.4 |
| XIV | 5.6 | 2.0 | 4.4 | 27.1 | 45.9 |
| XV | 26.6 | 19.5 | 15.4 | 27.5 | 50.2 |
| Non-acylated TETA succinimide | 48.6 | 19.4 | 13.0 | 30.4 | 60.6 |

[1]SAE 10W-40 motor oil formulations containing the indicated wt. % dispersant.

To further illustrate the utility of these hydroxyacylated succinimide dispersants, a SAE 30 motor oil formulation containing the product from Example VIII gave excellent results in Sequence V-D and Caterpillar 1H2 testing (Seq. V-D: Avg. Sludge—9.5; Avg. Varnish 7.4; PSV—7.6. Cat. 1H2: 2% TGF; 58 WTD.).

The foregoing tests demonstrate that the prescribed hydroxyacylated hydrocarbylsuccinimide of the invention is an excellent dispersant for a lubricating oil composition and is surprisingly effective for ameliorating or overcoming the rubber seal deterioration problem caused by nitrogen-containing dispersants.

We claim:

1. A hydrocarbyl-substituted mono- and bis-succinimide having polyamine chain linked hydroxyacyl radicals represented by the formula:

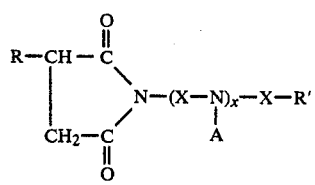

in which R is a hydrocarbyl radical having from about 8 to 400 carbon atoms, X is a divalent alkylene or secondary hydroxy substituted alkylene radical having from 2 to 3 carbon atoms, A is hydrogen or a hydroxyacyl radical selected from the group consisting of glycolyl, lactyl, 2-hydroxy-methyl propionyl and 2,2'-bis-hydroxymethyl propionyl radicals and in which at least 30 percent of said radicals represented by A are said hydroxyacyl radicals, x is a number from 1 to 6, and R' is a radical selected from the group consisting of —NH$_2$, —NHA, or a hydrocarbyl substituted succinyl radical having the formula:

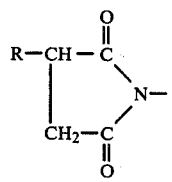

in which R and A have the values noted above.

2. A hydrocarbyl-substituted mono- and bis-succinimide according to claim 1 in which at least 50 percent of said radicals represented by A are hydroxyacyl radicals.

3. A hydrocarbyl-substituted mono- and bis-succinimide according to claim 1 in which substantially all of said radicals represented by A are hydroxyacyl radicals.

4. A hydrocarbyl-substituted mono- and bis-succinimide according to claim 1 in which at least 30 percent of said radicals represented by A are glycolyl radicals.

5. A hydrocarbyl substituted mono- and bis-succinimide according to claim 1 in which at least 30 percent of said radicals represented by A are lactyl radicals.

6. An alkenyl succinimide represented by the formula:

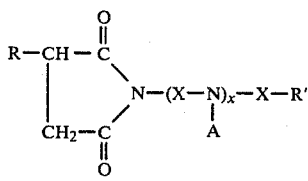

in which R is an alkenyl radical having from about 50 to 200 carbon atoms, X is a divalent —CH$_2$—CH$_2$—, or —CH$_2$—CHOH—CH$_2$—radical, A is hydrogen or a glycolyl radical in which 50 to 100 percent of said radicals represented by A is said glycolyl radical, x is a number from 2 to 4, and R' is a radical selected form the group consisting of —NH$_2$ and —NHA in which A has the value noted above.

7. An alkenyl succinimide represented by the formula:

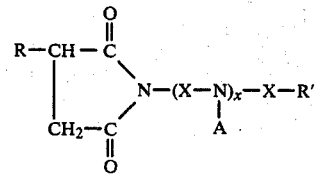

in which R is an alkenyl radical having from about 50 to 200 carbon atoms, X is a divalent —CH$_2$—CH$_2$—, or a divalent —CH$_2$—CHOH—CH$_2$—radical, A is hydrogen or a glycolyl radical in which at least 70 percent of said radicals represented by A are said glycolyl radical, x is a number from 2 to 4 and R' is a radical selected from the group consisting of —NH$_2$ and —NHA in which A has the value noted above.

8. An alkenyl succinimide according to claim 7 in which 85 to 100 percent of said radicals represented by A are glycolyl radicals.

9. A lubricant composition comprising a major proportion of an oil of lubricating viscosity and a minor dispersant amount of a hydrocarbyl-substituted mono- and bis-succinimide compound having branched hydroxyacyl radicals represented by the formula:

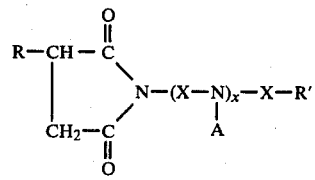

in which R is a hydrocarbyl radical having from about 8 to 400 carbon atoms, X is a divalent alkylene or secondary hydroxy substituted alkylene radical having from 2 to 3 carbon atoms, A is hydrogen or a hydroxyacyl radical selected from the group consisting of glycolyl, lactyl, 2-hydroxymethyl propionyl and 2,2'-bis-hydroxymethyl propionyl radicals and in which at least 30 percent of said radicals represented by A are said hydroxyacyl radicals, x is a number from 1 to 6, and R' is a radical selected from the group consisting of —NH$_2$, —NHA or a hydrocarbyl substituted succinyl radical having the formula:

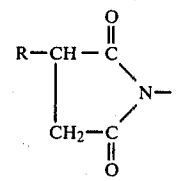

in which R and A have the values noted above.

10. A lubricant composition according to claim 9 in which at least 50 percent of said radicals represented by A in said succinimide are hydroxyacyl radicals.

11. A lubricant composition according to claim 9 in which substantially all of said radicals represented by A in said succinimide are hydroxyacyl radicals.

12. A lubricant composition according to claim 9 in which 50 to 100 percent of said radicals represented by A in said succinimide are glycolyl radicals.

13. A lubricant composition according to claim 9 in which at least 70 percent of said radicals represented by A in said succinimide are glycolyl radicals.

14. A lubricant composition according to claim 9 in which 50 to 100 percent of said radicals represented by A in said succinimide are lactyl radicals.

15. A lubricant composition according to claim 9 containing from about 0.01 to 10 weight percent of said compound.

16. A lubricant composition according to claim 9 containing from about 0.5 to 5 weight percent of said compound.

17. A mineral oil composition containing from about 0.001 to 80 weight percent of said mineral oil composition of the succinimide of claim 1.

* * * * *